(12) United States Patent
Nakaji (10) Patent No.: US 10,451,537 B2
(45) Date of Patent: Oct. 22, 2019

(54) DIFFUSING WAVE SPECTROSCOPY WITH HETERODYNE DETECTION

(71) Applicant: Canon U.S.A. Inc., Melville, NY (US)

(72) Inventor: Haruo Nakaji, Boston, MA (US)

(73) Assignee: Canon U.S.A., Inc., Melville, NY (US)

( * ) Notice: Subject to any disclaimer, the term of this patent is extended or adjusted under 35 U.S.C. 154(b) by 9 days.

(21) Appl. No.: 15/424,581

(22) Filed: Feb. 3, 2017

(65) Prior Publication Data

US 2017/0227445 A1   Aug. 10, 2017

Related U.S. Application Data

(60) Provisional application No. 62/291,264, filed on Feb. 4, 2016.

(51) Int. Cl.
| | | |
|---|---|---|
| *G01N 15/14* | (2006.01) | |
| *G01N 11/02* | (2006.01) | |
| *G01N 21/47* | (2006.01) | |
| *G01N 11/00* | (2006.01) | |

(52) U.S. Cl.
CPC ......... *G01N 15/1434* (2013.01); *G01N 11/00* (2013.01); *G01N 11/02* (2013.01); *G01N 15/1429* (2013.01); *G01N 21/474* (2013.01); *G01N 2011/008* (2013.01)

(58) Field of Classification Search
CPC .................. G01N 15/1429; G01N 15/1434
See application file for complete search history.

(56) References Cited

U.S. PATENT DOCUMENTS

| | | | |
|---|---|---|---|
| 6,037,579 A | 3/2000 | Chan et al. | |
| 6,076,010 A | 6/2000 | Boas et al. | |
| 6,432,054 B1 * | 8/2002 | Ustuner | G01S 7/52046 600/437 |
| 6,519,032 B1 * | 2/2003 | Kuebler | B01D 15/08 356/246 |
| 6,611,339 B1 | 8/2003 | Yang et al. | |

(Continued)

FOREIGN PATENT DOCUMENTS

| | | |
|---|---|---|
| DE | 102007045323 A1 | 4/2009 |
| WO | 98/21561 A1 | 5/1998 |
| WO | 2012143798 A1 | 10/2012 |

OTHER PUBLICATIONS

Lin, P., et al, "Non-invasive Optical Measurement of Cerebral Metabolism and Hemodynamics in Infants", Journal of Visualized Experiments, Mar. 2013, vol. 73.

(Continued)

*Primary Examiner* — Violeta A Prieto (74) *Attorney, Agent, or Firm* — Canon U.S.A., Inc. I.P. Division (57) ABSTRACT

Exemplary apparatus and methods are provided for analyzing a medium. The apparatus, which may be a diffusing wave spectroscopy apparatus, comprises a first beam splitter for splitting a light from the laser light source into an excitation light and a reference light. The excitation light is directed on to a first portion of the medium and then multiply scattered light is collected at a second portion of the medium, the second portion being different from the first portion. The reference light, which has been attenuated, is combined with the multiply scattered light and either a power spectrum or an autocorrelation function is calculated.

32 Claims, 8 Drawing Sheets

(56) References Cited

U.S. PATENT DOCUMENTS

| | | | |
|---|---|---|---|
| 6,819,420 B2* | 11/2004 | Kuebler | B01D 15/08 356/246 |
| 6,958,816 B1* | 10/2005 | Dogariu | G01N 11/02 356/479 |
| 8,082,015 B2 | 12/2011 | Yodh et al. | |
| 8,334,972 B2 | 12/2012 | Thien | |
| 8,692,990 B2 | 4/2014 | Matousek | |
| 8,810,796 B2 | 8/2014 | Hays et al. | |
| 2002/0101593 A1 | 8/2002 | Yang et al. | |
| 2003/0142309 A1* | 7/2003 | Kuebler | B01D 15/08 356/338 |
| 2006/0063995 A1 | 3/2006 | Yodh et al. | |
| 2008/0147339 A1 | 6/2008 | Ganz et al. | |
| 2010/0168586 A1 | 7/2010 | Hillman et al. | |
| 2011/0102776 A1* | 5/2011 | Hasegawa | G01M 11/3136 356/124.5 |
| 2013/0278749 A1 | 10/2013 | Mandelis et al. | |
| 2014/0206890 A1 | 7/2014 | Lee et al. | |
| 2014/0343384 A1 | 11/2014 | Floyd et al. | |
| 2015/0073271 A1 | 3/2015 | Lee et al. | |
| 2017/0194019 A1* | 7/2017 | Derrick | G10L 21/0364 |

OTHER PUBLICATIONS

Lin, P., et al., "Non-invasive Optical Measurement of Cerebral Metabolism and Hemodynamics in Infants," J. Vis. Exp., Mar. 14, 2013, vol. 73, e4379.

Carp, S., et al., "Due to intravascular multiple sequential scattering, Diffuse Correlation Spectroscopy of tissue primarily measures relative red blood cell motion within vessels", Biomed. Opt. Exp., Jul. 1, 2011, pp. 2047-2054, vol. 2, No. 7.

Yu, G., et al., "Near-Infrared Diffuse Correlation Spectroscopy for Assessment of Tissue Blood Flow", Handbook of Biomedical Optics, 2011, pp. 195-216, Chapter 10, CRC Press.

Dietsche, G. et al., "Fiber-based multispeckle detection for time-resolved diffusing-wave spectroscopy: characterization and application to blood flow detection in deep tissue", Applied Optics, 2007, pp. 8506-8514, vol. 46, No. 35.

Yu, G., et al., "Validation of diffuse correlation spectroscopy for muscle blood flow with concurrent arterial spin labeled perfusion MRI", Optics Express Feb. 5, 2007, pp. 1064-1075, vol. 15, No. 3.

He, L., et al., "Using optical fibers with different modes to improve the signal-to-noise ratio of diffuse correlation spectroscopy flow-oximeter measurements", Journal of Biomedical Optics, Mar. 2013, vol. 18, No. 3, 037001.

Pine, D.J., et al., "Diffusing-Wave Spectroscopy", Physical Review Letters, Mar. 21, 1988, pp. 1134-1137, vol. 60, No. 12.

Höhler, R., et al, "High-resolution diffusing-wave spectroscopy using optimized heterodyne detection", J. Opt. Soc. Am. A, Nov. 2003, pp. 2179-2184, vol. 20, No. 11.

Boas, D., et al., "Spatially varying dynamical properties of turbid media probed with diffusing temporal light correlation", J. Opt. Soc. Am. A, Jan. 1997, pp. 192-216, vol. 14, No 1.

* cited by examiner

DIFFUSING WAVE SPECTROSCOPY WITH HETERODYNE DETECTION

CROSS-REFERENCE TO RELATED APPLICATIONS

This application claims the benefit of U.S. Provisional Application No. 62/291,264, filed Feb. 4, 2016. U.S. Provisional Application No. 62/291,264, is hereby incorporated by reference.

FIELD OF THE DISCLOSURE

The present disclosure relates to optical spectroscopy. More particularly, the disclosure exemplifies diffusing wave spectroscopy

BACKGROUND INFORMATION

Diffusing wave spectroscopy (DWS) is the optical technique which studies the dynamics of a scattering medium by measuring multiply scattered light. The term of diffuse correlation spectroscopy (DCS) is used instead of DWS. Both work in the multiple scattering regimes. However, the term DCS has been extended to heterogeneous multiple-scattering media. For simplicity, the name of DWS is used herein and includes both techniques.

Figure 1:
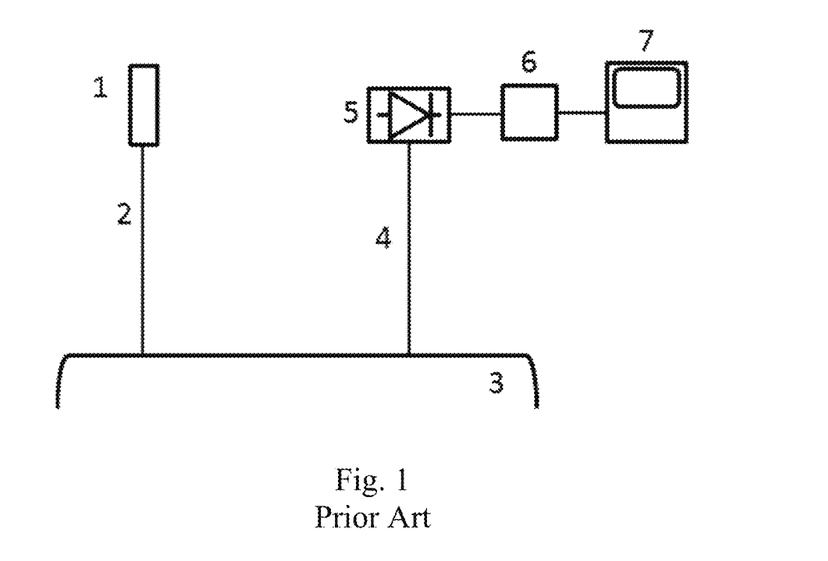
FIG. 1 shows a prior art example of a DWS system.

In general operation for a DWS system, a laser light source 1 outputs the laser light beam with long coherence length. For example, the coherence length of the laser light beam is about 10 m. The laser light source is coupled to a multimode fiber (MMF) 2. The light is irradiated to the sample 3 via the MMF 2. The irradiated light is multiply scattered in the sample 3. A part of the multiply scattered light is detected by a single mode fiber (SMF) or a few mode fiber 4. The distance between the MMF 2 and the SMF 4 depends on the depth of interest. The detected light is input to a photon-counting avalanche photodiode (APD) 5. The intensity autocorrelation function is calculated using the correlator 6 and processed in a computer 7. The DWS may have plural detection system. For example, see David A. Boas, et al., Handbook of Biomedical Optics, CRC Press, Chapter 10, 2011.

The decay time which is calculated from the intensity autocorrelation function is related to the viscosity of the sample and/or the flow of particles in the sample. Therefore, for example, DWS has been used for estimating blood flow in the tissue. See G. Dietsche, M. et al., Appl. Opt., Vol. 46, No. 35, 8506-8514, 2007.

However, the performance of DWS systems are significantly degraded by noise. One significant type of noise is dark current. The dark current is the electric current output from a detector without light input to the detector. Other sources of noise include light which comes from other light sources. Room light and the sunlight are typical noise light. The light emitted from another laser light source is also noise light and can be a significant source of noise in some applications of DWS. To reduce noise light, the measurement may be performed in a darkroom or when the detection system is shielded carefully. Also, the narrow optical bandpass filter can be used for decreasing the noise light. However, each of these solutions have their own drawbacks—such as requiring a darkroom in a doctor/patient setting.

In order to avoid the influence of dark current to DWS measurement, the photon-counting photomultiplier tube (PMT) or avalanche photo diode (APD) with low dark current (dark count rate) are often employed. In Dietsche et al., an APD with the maximum dark count rate of 500 cps (SPCM-AQ4C, PerkinElmer) was used. This system employed separate detection of plural speckle grains, plural intensity autocorrelation function curves that were calculated in parallel and averaged. By using this technique, the measurement time can be reduced. However, plural photon counting APDs and plural correlators were needed, adding significant cost and complexity to the system.

Thus, there is need for in DWS to provide a low noise system at a low cost.

SUMMARY OF EXEMPLARY EMBODIMENTS

According to at least one embodiment of the invention, there is provided a method and an apparatus. The method, which is a method for analyzing a medium comprises the steps: receiving a light from a light source, splitting the light into an excitation light and a reference light, wherein the intensity of the reference light is such that the coherence factor to root mean square (RMS) ratio is greater than 2 (or more preferably 3 or 5), irradiating a first portion of the medium with the excitation light, collecting a sample light from a second portion of the medium that is different from the first portion of the medium, wherein the sample light is from the excitation light multiply scattered in the medium, combining the reference light with the sample light, inputting the combined lights to an optical detector, and calculating a power spectrum or an autocorrelation function from a signal output from the optical detector.

Additional steps may include one or more of: attenuating the intensity of the reference light before combining the reference light with the sample light; adjusting the intensity of the reference light so that the intensity of the reference light at the detector is greater than a tenth part of a noise level and less than the saturation intensity of the optical detector; adjusting the intensity of the reference light so that the intensity of the reference light at the detector is almost equal to a noise level; calculating particle flow data from the power spectrum or autocorrelation function and optionally displaying or recording the particle flow data; and/or calculating viscosity data from the power spectrum or autocorrelation function and optionally displaying or recording the viscosity data.

Other embodiments provide an apparatus comprising: at least one laser light source, at least one first beam splitter for splitting a light from the laser light source into an excitation light and a reference light, wherein the intensity of the reference light is such that, when, in use, the coherence factor to root mean square (RMS) ratio is greater than 2 (or more preferably 3 or 5), at least one directing element for irradiating the excitation light at a first portion of the medium, a collecting element for collecting multiply scattered light referred to as sample light at a second portion of the medium, the second portion being different from the first portion, at least one second beam splitter for combining the sample light and the reference light, at least one detector for measuring the optical intensity of the combined light, at least one limiting element located between the medium and the optical detector, and at least one analyzer for calculating either a power spectrum or an autocorrelation function. The apparatus may optionally also include one or more elements for analyzing, saving, and/or displaying data such as particle flow data and further optionally calculating a viscosity.

The apparatus may attenuate the reference light relative to the excitation light via the beam splitter, or it may optionally comprise an attenuating element for attenuating the reference light. The attenuating element may be an optical attenuator.

The apparatus may be configured such that the excitation light has a greater intensity than the reference light, or where the intensity of the reference light at the detector is greater than a tenth part of a noise level and less than the saturation intensity of the optical detector, or where the intensity of the reference light at the detector is almost equal to a noise level. In some embodiments, the second beam splitter comprises at least two ports, wherein the sample light is input to a first port having a higher transmission and the reference light is input to a second port having a lower transmission. The limiting element may be defined as a pinhole or an optical fiber and the detector may be a lower-cost device such as a photon counting avalanche diode or photomultiplier tube.

In some embodiments, the apparatus as disclosed herein is configured as a diffusing wave spectroscopy apparatus that is designed for use as a medical device having, for example, a fiber-coupled laser light source, fiber optic couplers, and an optical detector.

These and other objects, features, and advantages of the present disclosure will become apparent upon reading the following detailed description of exemplary embodiments of the present disclosure, when taken in conjunction with the appended drawings, and provided claims.

BRIEF DESCRIPTION OF DRAWINGS

Further objects, features and advantages of the present disclosure will become apparent from the following detailed description when taken in conjunction with the accompanying figures showing illustrative embodiments of the present disclosure.

FIGS. 8(a)-8(d) are charts showing the dependence of coherence factor on reference light intensity. The noise levels were: FIG. 8(a) 0.01 kcps, FIG. 8(b) 3 kcps, FIG. 8(c) 30 kcps(c), and FIG. 8(d) 300 kcps.

FIGS. 9(a)-9(d) are charts showing the dependence of decay time on reference light intensity. The noise levels were: FIG. 9(a) 0.01 kcps, FIG. 9(b) 3 kcps, FIG. 9(c) 30 kcps(c), and FIG. 9(d) 300 kcps.

FIGS. 10(a)-10(d) are charts showing the dependence of the coherence factor to RMS ratio on the reference light intensity. The noise levels were: FIG. 10(a) 0.01 kcps, FIG. 10(b) 3 kcps, FIG. 10(c) 30 kcps, and FIG. 10(d) 300 kcps.

Throughout the figures, the same reference numerals and characters, unless otherwise stated, are used to denote like features, elements, components or portions of the illustrated embodiments. Moreover, while the subject disclosure will now be described in detail with reference to the figures, it is done so in connection with the illustrative exemplary embodiments. It is intended that changes and modifications can be made to the described exemplary embodiments without departing from the true scope and spirit of the subject disclosure as defined by the appended claims.

DETAILED DESCRIPTION OF EXEMPLARY EMBODIMENTS

Figure 2:
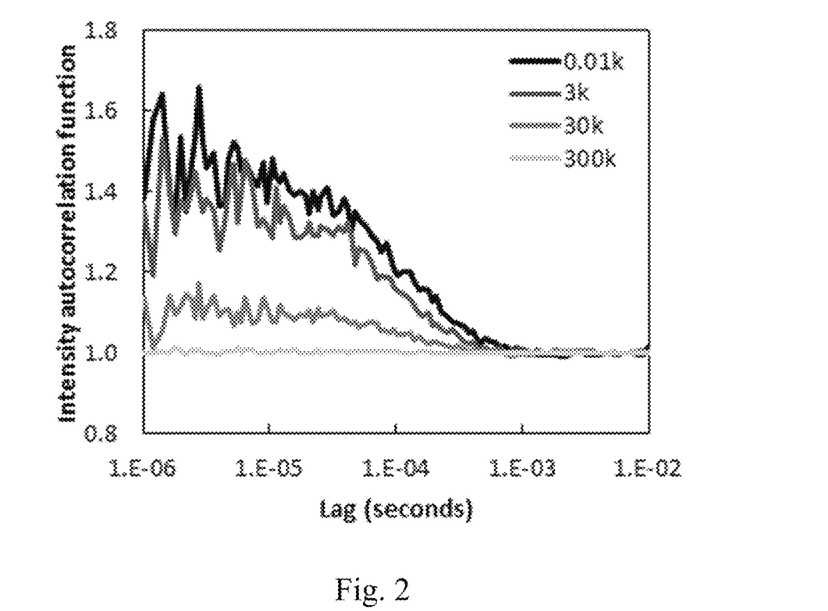
FIG. 2 Influence of the noise level to the intensity autocorrelation function curve.

Noise is a significant factor in the performance of DWS system. FIG. 2 shows the influence of noise level to the autocorrelation function curve in DWS system. For example, when the noise level increases from 0.01 kcps to 300 kcps, the intersection of the y-axis and the autocorrelation function curve is decreased. In the example of FIG. 2, the dark count rate of the APD was about 0.01 kcps. The noise level was changed from 0.01 kcps to 300 kcps by inputting the laser light beam which is output from another laser light source to the APD. The intensity of light which was multiply scattered in the sample and input to the APD was about 30 kcps. The sample consists of the 1% low-fat milk and water. The distance between the irradiation fiber and the detection fiber was 20 mm.

In order to analyze the influence of the noise level to the intensity autocorrelation function quantitatively, the measured intensity autocorrelation function $g_2(\tau)$ was fitted by using the following equation:

$$f_2(\tau) = 1 + \beta \cdot \exp(-\tau/\tau_c) \quad (1),$$

where $\beta$ is the coherence factor, $\tau$ is the lag, and $\tau_c$ is the decay time. The $\beta$ and $\tau_c$ of Eq. 1 were optimized so that the root-mean-square (RMS) was minimized. RMS was calculated by using the following equation:

$$\text{RMS} = \sqrt{\frac{1}{N}(g_2(\tau) - f_2(\tau))^2} \quad (2)$$

where $\tau$ is greater than $10^{-6}$ and smaller than the lag when $g_2(\tau)$ becomes 1.

Figure 3:
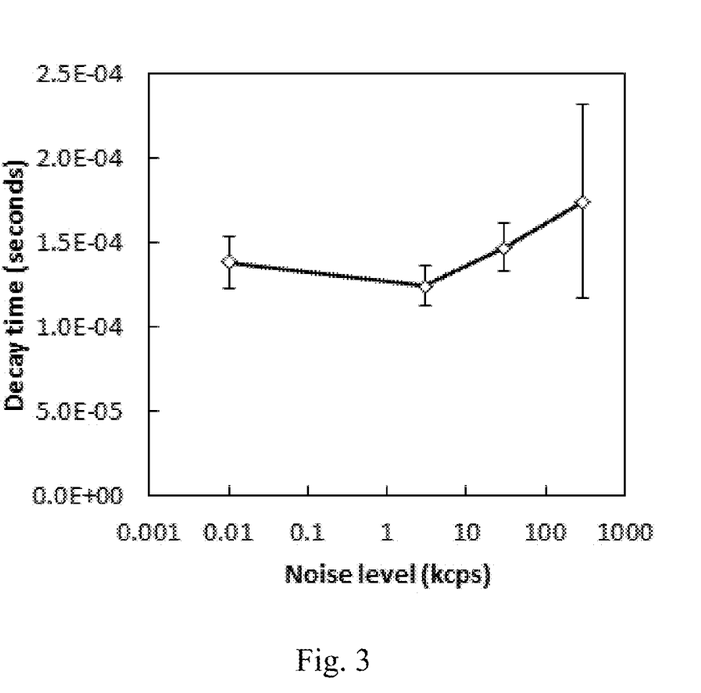
FIG. 3 shows a relation between the decay time and the noise level.

In DWS system, the viscosity of the sample or the flow of the moving particles in the sample can be estimated from the decay time $\tau_c$. FIG. 3 shows the relation between the decay time and the noise level. The error bars represent one standard deviation. The standard deviations were calculated from 10 measured decay times. The experimental conditions were the same with those of FIG. 2.

The standard deviation of decay time increased by increasing the noise level. If the standard deviation of measured decay times is large, the multiple curves should be acquired and averaged in order to improve the accuracy of measurement. In that case, the measurement time becomes longer. However, if the standard deviation of measured decay time is small, the measurement time is short because the averaging may not be necessary or the number of curves for averaging may be smaller.

Thus, there is provided an apparatus and method for DWS employing the heterodyne detection scheme and a method of optimizing the intensity of the reference light which is input to an optical detector together with the multiply scattered light in the medium.

In general, the heterodyne detection is a method of detecting radiation such as light by mixing with the radiation with the different frequency. To clarify the difference from conventional DWS systems, the heterodyne detection as described herein is defined as the scheme to mix the reference light and the scattered light (sample light) regardless of the frequencies.

Figure 4:
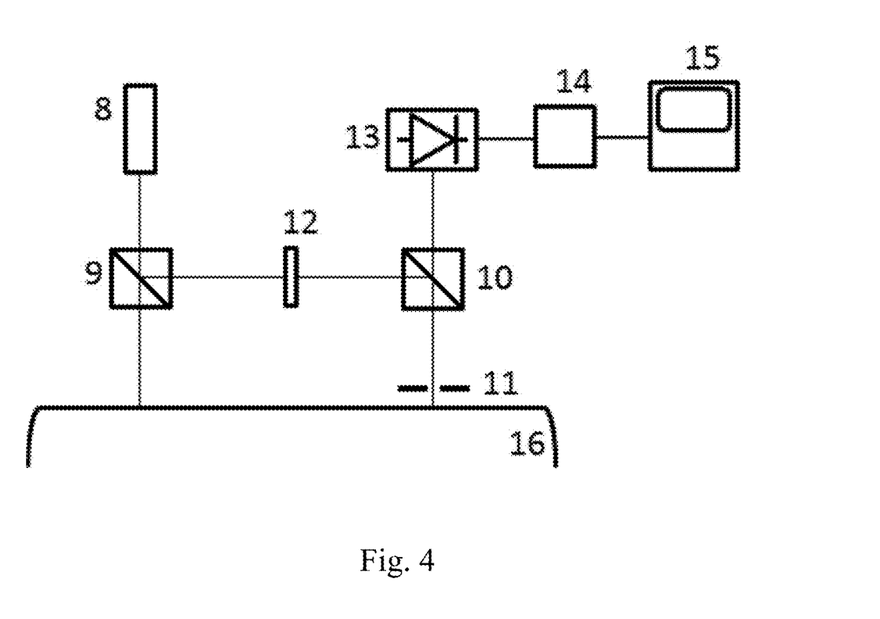
FIG. 4 shows the first embodiment of DWS system employing heterodyne detection scheme.

FIG. 4 shows the first embodiment of DWS system employing heterodyne detection scheme. The laser light source 8 outputs the laser light beam with long coherence length. The laser light beam is split by the first beam splitter 9 into two, where the two lights can be described as an excitation light and a reference light. The excitation light is irradiated to the medium 16. An optical diffuser can be located, for example, between the first beam splitter 9 and the medium 16 for laser safety. This excitation light will irradiate a certain portion of the medium 16. The light will then multiply scatter in the medium 16. In more detail, the excitation light, after hitting the first portion of the medium which may be, for example, a tissue including capillary vessels, will enter the capillary vessels.

Figure 5:
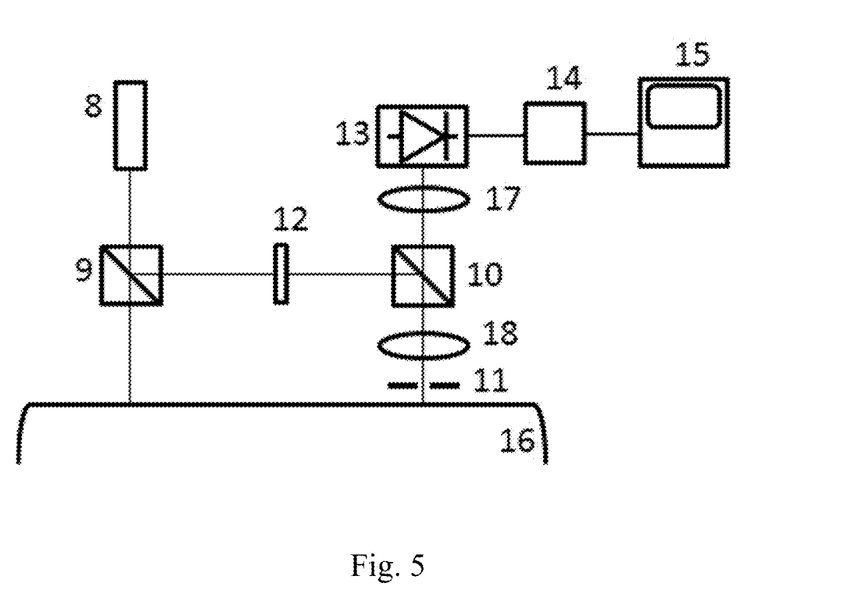
FIG. 5 shows another DWS system of the first embodiment employing heterodyne detection scheme.

Multiply scattered light (sample light) is then collected from a portion of the medium that is different from the irradiation position. Thus, these first and second portions of the medium are at different locations and may be separated by, for example, 1, 2, 3, 4, 5, 6, 7, 8, 9, 10 or more cm, center to center. The sample light is then delivered to the second beam splitter 10 via a pinhole 11. The reference light that was split by the first beam splitter 9 is input to the second beam splitter 10 via the optical attenuator 12. The sample and the reference lights are combined by the second beam splitter 10 and input to the optical detector 13. A pinhole 4 can be located between the medium 16 and the optical detector 13. In some embodiments, other limiting element(s) are used instead of a pinhole. For example an optical element such as an optical fiber may be used. Optionally, such as shown in the embodiment of FIG. 5, one or more lenses can be placed between the medium 16 and the optical detector 13. In the embodiment shown in FIG. 5, a lens 17 is located between the second beam splitter 10 and optical detector 13. Another lens 18 is located between the second beam splitter 10 and pinhole 11. One or both of these additional lens or lens systems may be used in this embodiment.

The signal output from the optical detector 13 is input to the correlator 14 for calculating an intensity autocorrelation function. The intensity autocorrelation function is analyzed, saved, and/or displayed at the computer 15. For example, the decay time is calculated from the intensity autocorrelation function. From the calculated decay time, the viscosity of the sample, the flow of the particles in the sample and so on can be calculated and displayed or saved. According to the Wiener-Khinchin theorem, the power spectrum of the process is equal to the Fourier transform of the autocorrelation function of the process. Therefore, the power spectrum can be calculated instead of the intensity autocorrelation function. After calculation of the power spectrum, properties such as e viscosity of the sample, the flow of the particles in the sample and so on can be calculated and displayed or saved by the computer 15.

A diode-pumped solid state (DPSS) laser, a distributed feedback (DFB) laser, an external cavity diode laser or a vertical cavity surface emitted laser (VCSEL) are particularly useful for the light source, or laser 8 of DWS system, because those lasers emit the laser light beam with long coherence length. A neutral density (ND) filter can be used as the optical attenuator 12. A photon-counting avalanche photodiode (APD) or photomultiplier tube (PMT) is suitable as the optical detector 13.

In general, the light which reaches the optical detector 13 via the medium 16, the pinhole 11 and the second beam splitter 10 is very weak. Thus, it is preferred to reduce the intensity of the reference light before inputting to the optical detector 13. It is suitable that the transmission from the laser 8 to the medium 16 is higher than that from the laser 8 to the optical attenuator 12. Also, it is suitable that the transmission from the medium 16 to the optical detector 13 is higher than that from the optical attenuator 12 to the optical detector 13.

Figure 6:
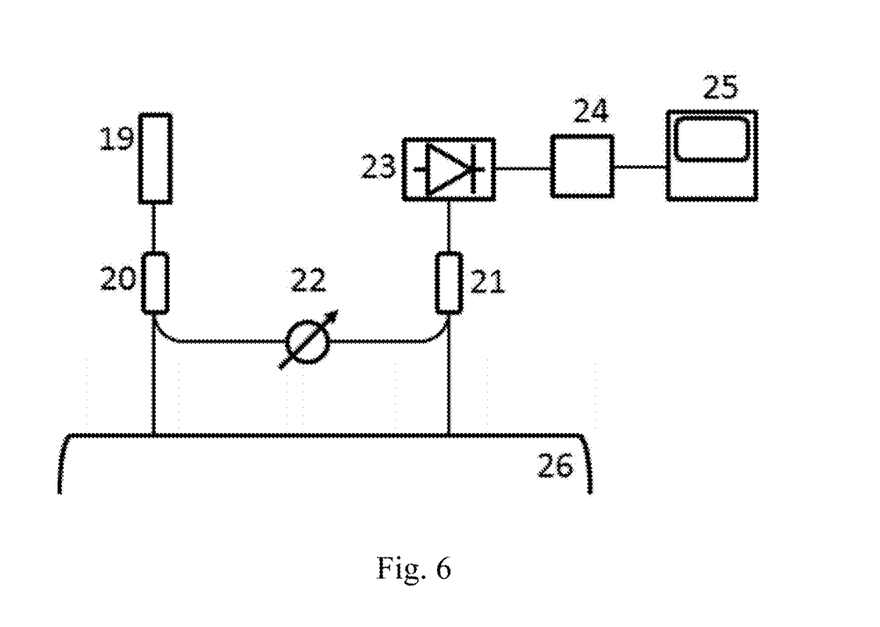
FIG. 6 shows the second embodiment of DWS system employing heterodyne detection scheme.

FIG. 6 shows a second embodiment of DWS system employing heterodyne detection scheme. The laser light source 19 emits the laser light beam with long coherence length. The laser light source 19 is coupled to the fiber. Although both a single mode fiber (SMF) and a multimode fiber (MMF) can be used, the SMF is more suitable for the embodiments as described herein. The laser light beam is input to the first fiber coupler 20 and split into two. The one laser light beam is irradiated to the medium 26. That light is multiply scattered in the medium 26. A part of the multiply scattered light is collected and delivered to the second fiber coupler 21 via an optical fiber. That optical fiber should be a SMF or a few-mode fiber. The other laser light beam split by the first fiber coupler 20 is delivered to the second fiber coupler 21 via the optical attenuator 22. The two light beams are combined by the second fiber coupler 21 and input to the optical detector 23. The signal output from the optical detector 23 is input to the correlator 24 for calculating an intensity autocorrelation function. The computer 25 saves, analyzes, and/or displays data.

A diode-pumped solid state (DPSS) laser, a distributed feedback (DFB) laser, an external cavity diode laser or a vertical cavity surface emitted laser (VCSEL) is suitable for the laser light source 19, because those laser emit a laser light beam with long coherence length. If the laser light source 19 is couple to the MMF, the first fiber coupler 20 is a multimode fiber coupler. If the laser light source 19 is coupled to the SMF, the first fiber optic coupler is a single mode fiber coupler. The SMF and the single mode fiber coupler are more suitable. Both fixed and variable optical attenuators can be used as the optical attenuator 22. The second fiber coupler 21 is a single mode fiber coupler or a few mode fiber coupler. A photon-counting avalanche photodiode (APD) or photomultiplier tube (PMT) is suitable as the optical detector 23. According to the Wiener-Khinchin theorem, the power spectrum of the process is equal to the Fourier transform of the autocorrelation function of the process. Therefore, the power spectrum can be calculated instead of the intensity autocorrelation function. For example, the computer calculates the decay time from the autocorrelation function and expects the viscosity of the medium and/or the flow of particles in the medium.

The embodiments shown in FIGS. 4, 5, and 6 have one detection system which consists of a beam splitter or a fiber coupler and an optical detector. However, plural detection systems can be employed in apparatus and methods as described herein. Such plural detection systems are exemplified by G. Dietsche, M. et al., Appl. Opt., Vol. 46, No. 35, 8506-8514, 2007, herein incorporated by reference.

In general, the light beam which reaches the optical detector 23 via the medium 26 and the second fiber coupler 21 (the sample light) is very weak. The intensity of the light beam which is input to the optical detector 23 via the optical attenuator 22 and the fiber coupler 21 (the reference light) is preferably substantially reduced. Therefore, it is suitable that the transmission from the laser 19 to the medium 26 is higher than that from the laser 19 to the optical attenuator 23. Also, it is suitable that the transmission from the medium 26 to the optical detector 23 is higher than that from the optical attenuator 22 to the optical detector 23.

The optical attenuator 22 or another attenuation device can be used to adjust the intensity of the reference light. For example, the reference light intensity can be adjusted such that, at the detector, it is greater than ⅒, or ⅕ of the noise level and less than the saturation intensity of the optical detector. The reference light intensity may be adjusted to be almost equal to the noise level. For example, the intensity of the reference light is within 10%, within 5%, within 3%, within 2%, within 1%, within 0.5% or less of the intensity of the noise. The noise level may essentially be due the dark current, or it may be the dark current, noise from room lights and/or stray light from the excitation source, interference, and also may include other types of noise. For calculation of noise levels, the noise level is the noise measured at the detector.

Figure 7:
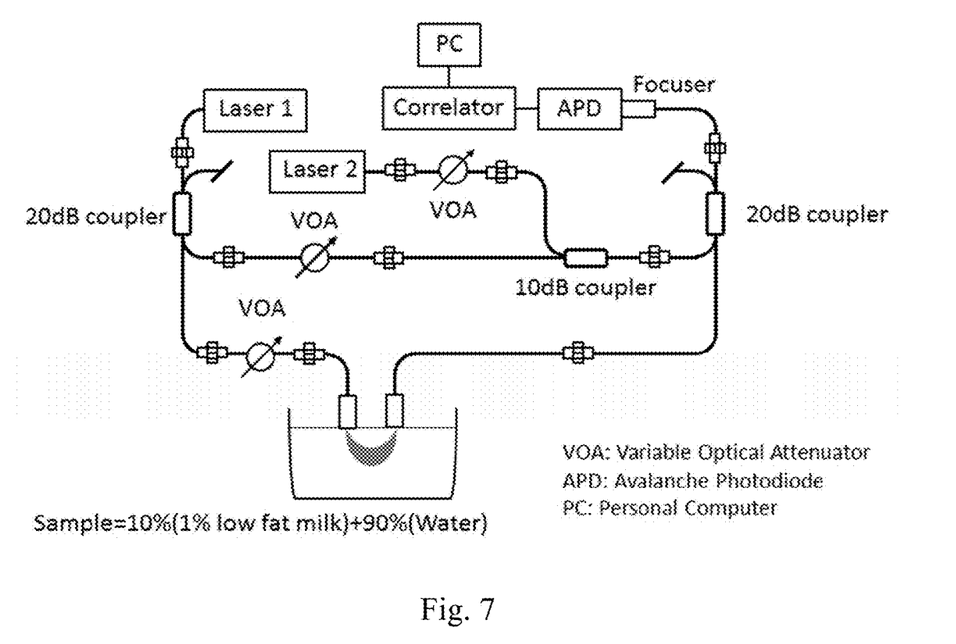
FIG. 7 shows an experimental setup for optimizing the reference light intensity.

In order to optimize the intensity of the reference light, the experiment was performed by using the experimental setup shown in FIG. 7.

The laser light beam is emitted from Laser 1 (CrystaLaser, DL785-100-SO) and input to the first 20 dB coupler. The laser light beam is split by the first 20 dB fiber coupler. One laser light beam is irradiated to the sample. That light is multiply scattered in the sample. A part of the multiply scattered light is collected by a SMF. That light is referred to as a sample light. The sample light is delivered to the second 20 dB fiber coupler. The other laser light beam split by the first 20 dB fiber coupler is referred to as a reference light. The reference right is delivered to the second 20 dB fiber coupler via the variable optical attenuator and the 10 dB fiber coupler. The sample light and the reference light are combined by the second 20 dB fiber coupler and delivered to the photon counting APD (Hamamatsu Photonics, C11202-100). The dark count rate of the photon-counting APD was about 0.01 kcps. In order to change noise level, the laser light beam output from Laser 2 (Thorlabs, LDM785) is input to the photon counting APD via the 10 dB fiber coupler, the 20 dB fiber coupler, and the focuser. That laser light is referred to as a noise light. The intensities of the sample, reference, and noise light at the photon counting APD were adjusting by using variable optical attenuators (VOAs). The experimental setup shown in FIG. 7 consists of SMFs. The sample consists of 1% low fat milk and water. The correlator calculates an intensity autocorrelation function from the signal output from the photon counting APD.

The measured intensity autocorrelation function $g_2(\tau)$ was fitted by using the following equation:

$$f_2(\tau) = 1 + \beta \cdot \exp(-\tau/\tau_c) \quad (3),$$

where $\beta$ is the coherence factor, $\tau$ is the lag, and $\tau_c$ is the decay time. The coherence factor is equal to the intersection of y-axis and the intensity autocorrelation function.

$\beta$ and $\tau_c$ of Eq. 1 were optimized so that the root-mean-square (RMS) was minimized. RMS was calculated by using the following equation:

$$\text{RMS} = \sqrt{\frac{1}{N}(g_2(\tau) - f_2(\tau))^2}, \quad (4)$$

where $\tau$ is greater than $10^{-6}$ and smaller than the lag when $g_2(\tau)$ becomes 1.

The minimum lag of the measured intensity autocorrelation function for this embodiment was $2 \times 10^{-7}$ seconds. The values of the intensity autocorrelation function around the minimum lag were too noisy. On the other hand, the value of intensity autocorrelation approaches to 1 by increasing the lag. Therefore, the interval for calculating RMS was set from $1 \times 10^{-6}$ and the lag when $g_2(\tau)$ becomes 1.

Figure 8A:
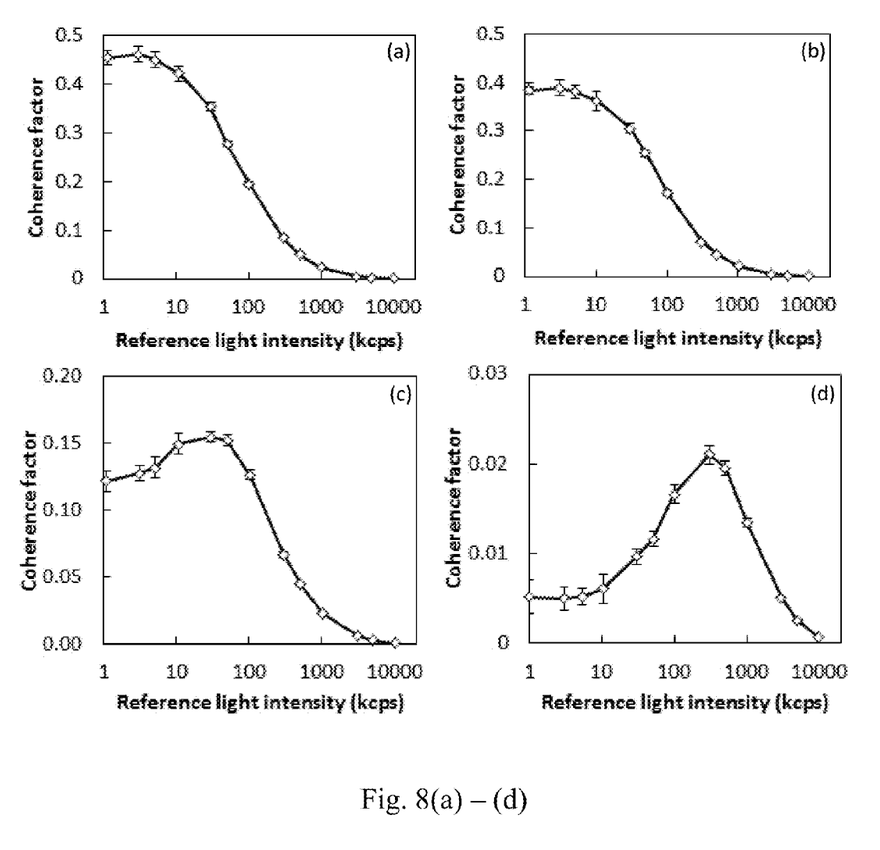

FIG. 8 shows the dependence of coherence factor on reference light intensity. The noise levels were (a) 0.01 kcps, (b) 3 kcps, (c) 30 kcps, and (d) 300 kcps. The error bars represent one standard deviation. The standard deviations were calculated from 10 measured intensity autocorrelation function curves.

FIG. 8 shows the dependence of coherence factor on reference light intensity. When the noise levels were about 0.01 kcps and 3 kcps, the coherence factor decreased by increasing the reference light intensity. When the noise levels were about 30 kcps and 300 kcps, the coherence factor increased until the reference light intensity was almost equal to the noise level. When the reference light intensity was greater than the noise level and the noise levels were about 30 kcps and 300 kcps, the coherence factor decreased by increasing the reference light intensity. On the other word, when the noise levels were about 30 kcps and 300 kcps, the coherence factor was maximized at the reference light intensity which is almost equal to the noise level. In FIGS. 8 (c) and (d), the increase of the coherence factor started at the reference light intensity which was almost equal to a tenth part of the noise level. Therefore, it is suitable that the reference light intensity is greater than a tenth part of the noise level, because the increase of coherence factor starts. Also it is suitable that reference light intensity is almost equal to the noise level, because the coherence factor is maximized.

Figures 9A, 9D:
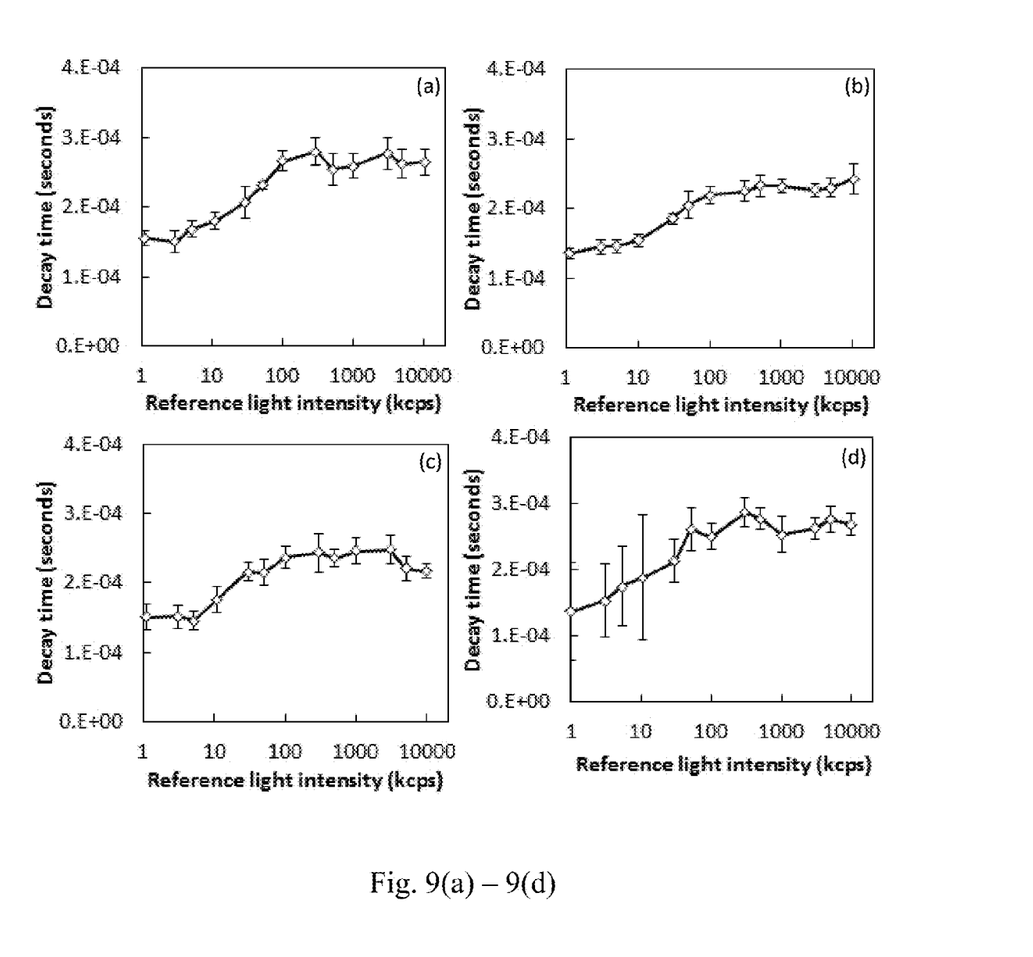

FIG. 9 shows the dependence of decay time on reference light intensity. The noise levels were (a) 0.01 kcps, (b) 3 kcps, (c) 30 kcps, and (d) 300 kcps. The error bars represent one standard deviation. The standard deviations were calculated from 10 measured decay times. In this example, regardless of the noise levels, the decay time was increased by increasing the reference light intensity. When the noise levels were about 0.01 kcps, 3 kcps, and 30 kcps, the standard deviations of decay time were small regardless of the reference light intensity. However, when the noise level was about 300 kcps, the standard deviation of decay time was decreased dramatically by changing the reference light intensity from about 10 kcps to 30 kcps. The decrease of the standard deviation of decay time and the beginning of the increase of coherence factor were occurred at the same reference light intensity. Although the decay time was increased by increasing the reference light intensity, the standard deviation of decay time remained small. The saturation intensity of the photon counting APD used in this experiment was about 20 Mcps. Therefore, it is suitable that the reference light intensity is greater than a tenth part of the noise level and smaller than the saturation intensity of the photon counting APD.

Figures 10A, 10D:
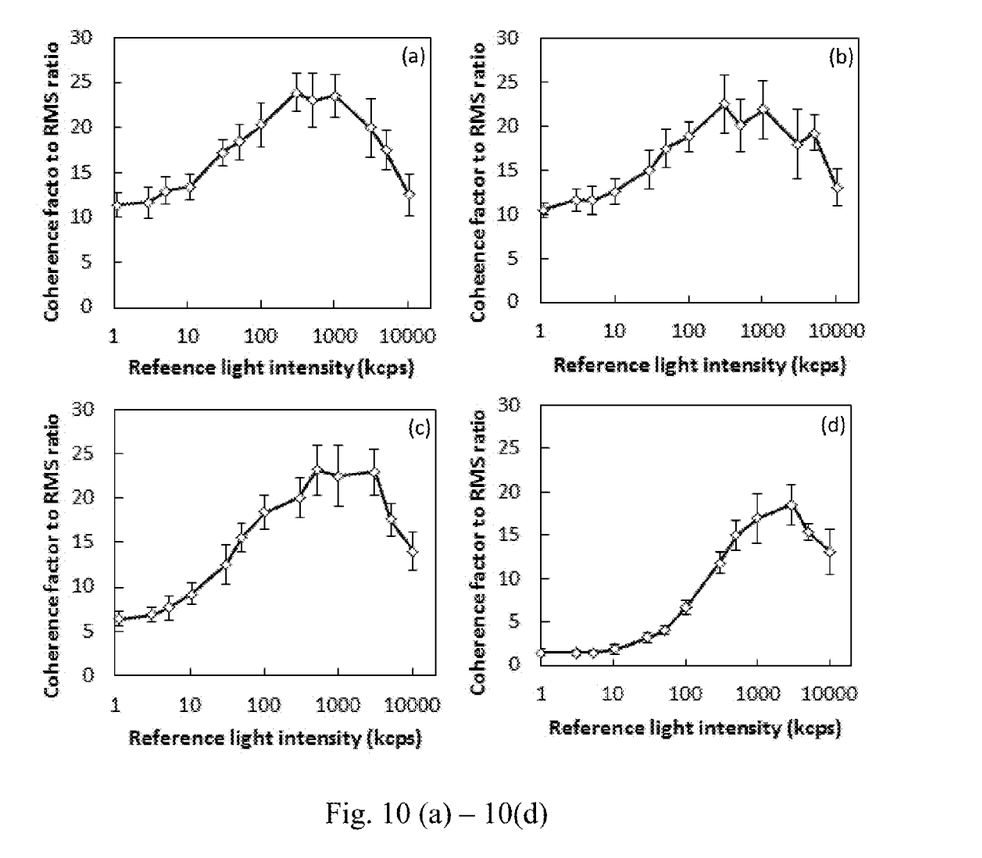

FIG. 10 shows the dependence of the coherence factor to RMS ratio on the reference light intensity. The noise levels were (a) 0.01 kcps, (b) 3 kcps, (c) 30 kcps (c), and (d) 300 kcps. The error bars represent one standard deviation. The standard deviations were calculated from 10 measured decay times.

The parameter which is the coherence factor to RMS ratio is introduced in order to demonstrate the effectiveness of heterodyne detection scheme in DWS system. FIG. 10 shows the dependence of the coherence factor to RMS ratio. When the noise level was about 300 kcps and the reference light intensity was change from about 10 kcps to about 30 kcps, the increase of the coherence factor was started and the standard deviation of decay time was dramatically decreased. According to FIG. 10d, when the reference light intensity was changed from 10 kcps to 30 kcps, the coherence factor to RMS ratio exceeded 3. When the noise levels were 0.01 kcps, 3 kcps, and 30 kcps, the coherence factor to RMS ratio exceeded 3 and the standard deviations of decay time were small at all reference light intensities.

Figure 11:
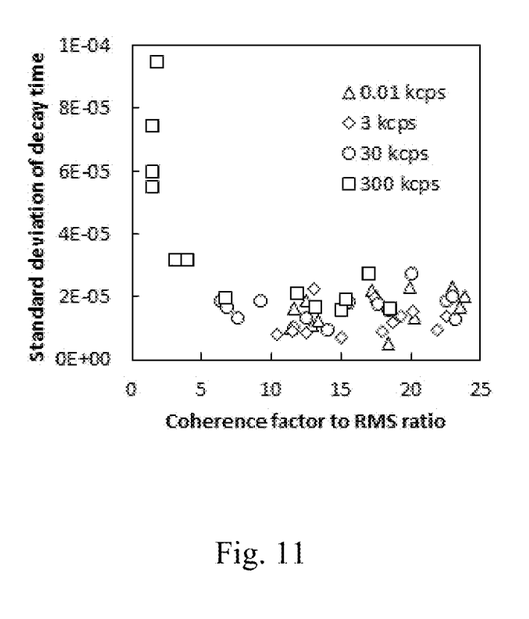
FIG. 11 is a chart showing the dependence of the standard deviation of decay time with the ration of coherence factor to RMS ratio. The noise levels were: 0.01 k, 3 k, 30 k, and 300 k cps.

In some embodiments, the intensity of the reference light is adjusted so that the coherence factor to root mean square (RMS) ratio is greater than 1, 2, 3, 4, 5, 7, or 10. The upper limit of the ratio is limited by the intensity of reference light and the saturation levels of the detector, and may be, for example, 25. Although the ratio increases, saturates, and then decreases by increasing the reference light intensity, the reference light intensity can be set so that the ratio exceeds 3. The various ratios demonstrated for different reference light intensities are shown in FIG. 11.

The coherence factor and the root mean square can be calculated using the following steps: (a) calculating an intensity autocorrelation function curve $g_2(\tau)$ from the measured data, and (b) fitting the intensity autocorrelation function and optimizing the coherence factor and the decay time so that the root mean square RMS is minimized. The autocorrelation function can be determined using equations (3) and (4) as described above where the root mean square is calculated over the interval $\tau_1 \leq \tau \leq \tau_2$, where $\tau_1$ is close or equal to the minimum lag and $\tau_2$ is the lag when the intensity autocorrelation function curve is close or equal to 1.

The intensity autocorrelation function $g_2(\tau)$ is the degree of second-order coherence. The degree of second-order coherence is expressed by using the degree of first-order coherence $g_1(\tau)$:

$$g_2(\tau) = 1 + |g_1(\tau)|^2 \quad (5)$$

The degree of coherence is related to the coherence of a laser light. In the other word, the degree of coherence is related to a line broadening of laser light. The dominant effects of the line broadening are the Doppler and collision broadening. The degree of first-order coherence for collision and Doppler broadened lights are followings:

$$g_1(\tau) = e^{-i\omega_0 \tau - (\tau/\tau_0)} \text{ for collision broadened light,} \quad (6)$$

$$g_1(\tau) = e^{-i\omega_0 \tau - \frac{\pi}{2}(\tau/\tau_0)^2} \text{ for Doppler broadened light.} \quad (7)$$

The measured intensity autocorrelation function curves in this experiment could be fitted very well by using Eq. 1.

$$f_2(\tau) = 1 + \beta \cdot \exp(-\tau/\tau_c) \quad (1)$$

It seems that the laser light in the sample, which was milk in this experiment, is broadened by the collision broadening effect dominantly. However, the multiply scattered laser light may be broadened by Doppler broadening effect dominantly. In that case, the equation for fitting may be needed to change to the following equation:

$$f_2(\tau) = 1 + \beta \cdot \exp(-\tau/\tau_c)^2 \quad (8)$$

See, for example, Rodney Loudon, The Quantum Theory of Light, Oxford University Press 3$^{rd}$ Edition, 2000.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). This is exemplified above as a computer and, optionally, also the correlator. The computer may comprise one or more processors (e.g., central processing unit (CPU), micro processing unit (MPU)) and may include a network of separate computers or separate processors to read out and execute the computer executable instructions. The computer may be a personal computer, a tablet device, or other dedicated processor, and may be integrally formed with the correlator. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like. An I/O interface can be used to provide communication interfaces to input and output devices, which may include a keyboard, a display, a mouse, a touch screen, touchless interface (e.g., a gesture recognition device) a printing device, a light pen, an optical storage device, a scanner, a microphone, a camera, a drive, communication cable and a network (either wired or wireless).

The detector interface also provides communication interfaces to input and output devices. The detector may include, for example a photomultiplier tube (PMT), a photodiode, an avalanche photodiode detector (APD), a charge-coupled device (CCD), multi-pixel photon counters (MPPC), or other. Also, the function of detector may be realized by computer executable instructions (e.g., one or more programs) recorded on a Storage/RAM.

Definitions

In referring to the description, specific details are set forth in order to provide a thorough understanding of the examples disclosed. In other instances, well-known methods, procedures, components and circuits have not been described in detail as not to unnecessarily lengthen the present disclosure.

It should be understood that if an element or part is referred herein as being "on", "against", "connected to", or "coupled to" another element or part, then it can be directly on, against, connected or coupled to the other element or part, or intervening elements or parts may be present. In contrast, if an element is referred to as being "directly on", "directly connected to", or "directly coupled to" another element or part, then there are no intervening elements or parts present. When used, term "and/or", includes any and all combinations of one or more of the associated listed items, if so provided.

Spatially relative terms, such as "under" "beneath", "below", "lower", "above", "upper", "proximal", "distal", and the like, may be used herein for ease of description to describe one element or feature's relationship to another element(s) or feature(s) as illustrated in the various figures. It should be understood, however, that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, a relative spatial term such as "below" can encompass both an orientation of above and below. The device may be otherwise oriented (rotated 90 degrees or at other orientations) and the spatially relative descriptors used herein are to be interpreted accordingly. Similarly, the relative spatial terms "proximal" and "distal" may also be interchangeable, where applicable.

The term "about," as used herein means, for example, within 10%, within 5%, or less. In some embodiments, the term "about" may mean within measurement error.

The terms first, second, third, etc. may be used herein to describe various elements, components, regions, parts and/or sections. It should be understood that these elements, components, regions, parts and/or sections should not be limited by these terms. These terms have been used only to distinguish one element, component, region, part, or section from another region, part, or section. Thus, a first element, component, region, part, or section discussed below could be termed a second element, component, region, part, or section without departing from the teachings herein.

The terminology used herein is for the purpose of describing particular embodiments only and is not intended to be limiting. As used herein, the singular forms "a", "an", and "the", are intended to include the plural forms as well, unless the context clearly indicates otherwise. It should be further understood that the terms "includes" and/or "including", when used in the present specification, specify the presence of stated features, integers, steps, operations, elements, and/or components, but do not preclude the presence or addition of one or more other features, integers, steps, operations, elements, components, and/or groups thereof not explicitly stated.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

While the present disclosure has been described with reference to exemplary embodiments, it is to be understood that the present disclosure is not limited to the disclosed exemplary embodiments. The scope of the following claims is to be accorded the broadest interpretation so as to encompass all such modifications and equivalent structures and functions.

What is claimed is:

1. A method for analyzing a medium comprising:
   receiving a light from a light source,
   splitting, via a first optical element, the light into an excitation light and a reference light,
   irradiating, via a directing element that receives the excitation light after the splitting step, a first portion of the medium with the excitation light,
   collecting, via a collecting element that is spaced away and separate from the directing element, a sample light from a second portion of the medium that is different from the first portion of the medium, wherein the sample light is from the excitation light multiply scattered in the medium,
   combining, via a second optical element that is spaced away and separate from the first optical element, the reference light with the sample light, wherein the second optical element receives the sample light from the collecting element after the collecting step,
   inputting the combined lights to an optical detector, and
   measuring or calculating a power spectrum or an intensity autocorrelation function from a signal output from the optical detector,
   wherein an intensity of the reference light is such that, when in use, a ratio of an intersection of a y-axis and the measured or calculated intensity autocorrelation function to a root mean square (RMS) is greater than 2.

2. The method of claim 1, wherein the ratio is greater than 3.

3. The method of claim 1, further comprising a step of attenuating the intensity of the reference light before combining the reference light with the sample light.

4. The method of claim 1, further comprising adjusting the intensity of the reference light so that the intensity of the reference light at the detector is greater than a tenth part of a noise level and less than the saturation intensity of the optical detector.

5. The method of claim 1, further comprising adjusting the intensity of the reference light so that the intensity of the reference light at the detector is almost equal to a noise level.

6. The method of claim 1, further comprising calculating particle flow data from the power spectrum or autocorrelation function and optionally displaying or recording the particle flow data.

7. The method of claim 1, further comprising calculating viscosity data from the power spectrum or intensity autocorrelation function and optionally displaying or recording the viscosity data.

8. The method of claim 1, wherein one or more of:
   (i) the measured or calculated intensity autocorrelation function is a measured intensity autocorrelation function $g_2(\tau)$ that is fitted using the following equation:

$$f_2(\tau) = 1 + \beta \cdot \exp(-\tau/\tau_c),$$

where $\beta$ is the intersection of the y-axis and the measured or calculated intensity autocorrelation function, $\tau$ is the lag, and $\tau_c$ is the decay time;
   (ii) the intersection of the y-axis and the measured or calculated intensity autocorrelation function $\beta$ and the decay time $\tau_c$ are optimized so that the RMS is minimized; and
   (iii) the RMS is calculated using the following equation:

$$\mathrm{RMS} = \sqrt{\frac{1}{N}(g_2(\tau) - f_2(\tau))^2},$$

where the root mean square is calculated over an interval $\tau_1 \leq \tau \leq \tau_2$, where $\tau_1$ is different from, or close or equal to, the minimum lag and $\tau_2$ is a lag when the intensity autocorrelation function curve is close or equal to 1, and N represents a number of sampling between $\tau_1$ and $\tau_2$.

9. The method of claim 1, wherein respective centers of the first portion and the second portion of the medium are separated and spaced away by one of: 1 cm, 2 cm, 3 cm, 4 cm, 5 cm, 6 cm, 7 cm, 8 cm, 9 cm, and 10 cm.

10. An apparatus for analyzing a medium comprising:
    at least one laser light source,
    at least one first beam splitter for splitting a light from the laser light source into an excitation light and a reference light, at least one directing element for irradiating the excitation light from the at least one first beam splitter at or to a first portion of the medium, a collecting element for collecting multiply scattered light referred to as sample light at a second portion of the medium, the second portion being different from the first portion and the collecting element being spaced away and separate from the at least one directing element, at least one second beam splitter for combining the sample light and the reference light, the at least one second beam splitter being spaced away and separate from the at least one first beam splitter, and the at least one second beam splitter operating to receive the collected sample light from the collecting element, at least one detector for measuring the optical intensity of the combined light, at least one limiting element located between the medium and the optical detector, and at least one analyzer for measuring or calculating either a power spectrum or an intensity autocorrelation function, wherein an intensity of the reference light is such that a ratio of an intersection of a y-axis and the measured or calculated intensity autocorrelation function to a root mean square (RMS) is greater than 2.

11. The apparatus of claim 10, wherein the ratio is greater than 3.

12. The apparatus of claim 10, further comprising an attenuating element for attenuating the reference light.

13. The apparatus of claim 12, wherein the attenuating element is an optical attenuator.

14. The apparatus of claim 10, wherein the apparatus is configured such that the excitation light has a greater intensity than the reference light.

15. The apparatus of claim 10, wherein the apparatus is configured such that the intensity of the reference light at the detector is greater than a tenth part of a noise level and less than the saturation intensity of the optical detector.

16. The apparatus of claim 10, wherein the apparatus is configured such that the intensity of the reference light at the detector is almost equal to a noise level.

17. The apparatus of claim 10, wherein the second beam splitter comprises at least two ports, wherein the sample light is input to a first port having a higher transmission and the reference light is input to a second port having a lower transmission.

18. The apparatus of claim 10, wherein the limiting element is a pinhole or an optical fiber.

19. The apparatus of claim 10, further comprising one or more elements for analyzing, saving, and/or displaying data.

20. The apparatus of claim 10, wherein the analyzer is configured to calculate a viscosity from either the power spectrum or intensity autocorrelation function.

21. The apparatus of claim 10, wherein one or more of:
(i) the measured or calculated autocorrelation function is a measured intensity autocorrelation function $g_2(\tau)$ that is fitted using the following equation:

$$f_2(\tau)=1+\beta \cdot \exp(-\tau/\tau_c),$$

where $\beta$ is the intersection of the y-axis and the measured or calculated intensity autocorrelation function, $\tau$ is the lag, and $\tau_c$ is the decay time;

(ii) the intersection of the y-axis and the measured or calculated intensity autocorrelation function $\beta$ and the decay time $\tau_c$ are optimized so that the RMS is minimized; and (iii) the RMS is calculated using the following equation:

$$\text{RMS} = \sqrt{\frac{1}{N}(g_2(\tau) - f_2(\tau))^2},$$

where the root mean square is calculated over an interval $\tau_1 \le \tau \le \tau_2$, where $\tau_1$ is different from, or close or equal to, the minimum lag and $\tau_2$ is a lag when the intensity autocorrelation function curve is close or equal to 1, and N represents a number of sampling between $\tau_1$ and $\tau_2$.

22. The apparatus of claim 10, wherein respective centers of the first portion and the second portion of the medium are separated and spaced away by one of: 1 cm, 2 cm, 3 cm, 4 cm, 5 cm, 6 cm, 7 cm, 8 cm, 9 cm, and 10 cm.

23. A diffusing wave spectroscopy apparatus for analyzing a medium comprising:
a fiber-coupled laser light source,
a first fiber optic coupler for splitting a light from the laser light source into an excitation light and a reference light,
a directing element for irradiating the excitation light from the first fiber optic coupler at or to a first portion of the medium,
a collecting element for collecting multiply scattered light referred to as sample light at a second portion of the medium, the second portion being different from the first portion and the collecting element being spaced away and separate from the directing element,
an attenuating element for attenuating the reference light,
a second fiber optic coupler for combining the sample light and the reference light, the second fiber optic coupler being spaced away and separate from the first fiber optic coupler, and the second fiber optic coupler operating to receive the collected sample light from the collecting element,
a limiting element located between the medium and the optical detector,
an optical detector for measuring the optical intensity of the combined light, and
an analyzer for measuring or calculating either a power spectrum or an intensity autocorrelation function,
wherein an intensity of the reference light is such that a ratio of an intersection of a y-axis and the measured or calculated intensity autocorrelation function to a root mean square (RMS) is greater than 2.

24. The diffusing wave spectroscopy apparatus of claim 23, wherein the ratio is greater than 3.

25. The diffusing wave spectroscopy apparatus of claim 23, wherein the attenuating element an optical attenuator.

26. The diffusing wave spectroscopy apparatus of claim 23, wherein the diffusing wave spectroscopy apparatus is configured such that the intensity of the reference light at the detector is greater than a tenth part of a noise level and less than the saturation intensity of the optical detector.

27. The diffusing wave spectroscopy apparatus of claim 23, wherein the diffusing wave spectroscopy apparatus is configured such that the intensity of the reference light at the detector is almost equal to a noise level.

28. The diffusing wave spectroscopy apparatus of claim 23, wherein the first fiber optic coupler comprises at least two ports with different transmissions, the excitation light is output from a first port of having a transmission that is higher than 50% and the reference light is output from a second port having a transmission that is less than 50%, and wherein the second fiber optic coupler comprises at least two ports with different transmissions, the sample light is output from a first port having a transmission that is higher than 50% and the reference light is output from a second port having a transmission that is less than 50%.

29. The diffusing wave spectroscopy apparatus of claim 23, wherein the limiting element is an optical fiber.

30. The diffusing wave spectroscopy apparatus of claim 23, wherein the analyzer is configured to calculate a viscosity from either the power spectrum or intensity autocorrelation function.

31. The diffusing wave spectroscopy apparatus of claim 23, wherein one or more of:
   (i) the measured or calculated autocorrelation function is a measured intensity autocorrelation function $g_2(\tau)$ that is fitted using the following equation:

$f_2(\tau)=1+\beta \cdot \exp(-\tau/\tau_c)$, where $\beta$ is the intersection of the y-axis and the measured or calculated intensity autocorrelation function, $\tau$ is the lag, and $\tau_c$ is the decay time;

(ii) the intersection of the y-axis and the measured or calculated intensity autocorrelation function $\beta$ and the decay time $\tau_c$ are optimized so that the RMS is minimized; and (iii) the RMS is calculated using the following equation:

$$\text{RMS} = \sqrt{\frac{1}{N}(g_2(\tau) - f_2(\tau))^2},$$

where the root mean square is calculated over an interval $\tau_1 \leq \tau \leq \tau_2$, where $\tau_1$ is different from, or close or equal to, the minimum lag and $\tau_2$ is a lag when the intensity autocorrelation function curve is close or equal to 1, and N represents a number of sampling between $\tau_1$ and $\tau_2$.

32. The diffusing wave spectroscopy apparatus of claim 23, wherein respective centers of the first portion and the second portion of the medium are separated and spaced away by one of: 1 cm, 2 cm, 3 cm, 4 cm, 5 cm, 6 cm, 7 cm, 8 cm, 9 cm, and 10 cm.

* * * * *